US012806434B2

(12) United States Patent
Lu et al.

(10) Patent No.: US 12,806,434 B2
(45) Date of Patent: Nov. 24, 2026

(54) PROTOCOL TO ENHANCE THERAPEUTIC EFFECTS OF TRANSCRANIAL MAGNETIC STIMULATION

(71) Applicant: The United States of America, as represented by the Secretary, Department of Health and Human Services, Bethesda, MD (US)

(72) Inventors: Hanbing Lu, Ellicott City, MD (US); Qinglei Meng, Catonsville, MD (US); Hieu Nguyen, Baltimore, MD (US); Yihong Yang, Ellicott City, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 954 days.

(21) Appl. No.: 18/076,071

(22) Filed: Dec. 6, 2022

(65) Prior Publication Data

US 2023/0173294 A1 Jun. 8, 2023

Related U.S. Application Data

(60) Provisional application No. 63/286,229, filed on Dec. 6, 2021.

(51) Int. Cl.
*A61N 2/02* (2006.01)
*A61N 2/00* (2006.01)

(52) U.S. Cl.
CPC ............... *A61N 2/02* (2013.01); *A61N 2/006* (2013.01)

(58) Field of Classification Search
CPC . A61N 2/02; A61N 2/006; A61N 2/00; A61N 2/002; A61N 2/004; A61N 2/008
See application file for complete search history.

(56) References Cited

U.S. PATENT DOCUMENTS 9,345,901 B2 5/2016 Peterchev
11,839,455 B2 12/2023 Williams et al.
(Continued)

FOREIGN PATENT DOCUMENTS

WO WO-9747352 A1 * 12/1997 ............... A61N 1/20

OTHER PUBLICATIONS

Cole et al., "Stanford Accelerated Intelligent Neuromodulation Therapy for Treatment-Resistant Depression," *Am. J. Psychiatry*, 177:8: 716-726 (2020).
(Continued)

*Primary Examiner* — Alex M Valvis
*Assistant Examiner* — Lara Linh Tran
(74) *Attorney, Agent, or Firm* — Leydig, Voit & Mayer

(57) ABSTRACT

A system for administering transcranial magnetic stimulation to a subject is provided. The system includes a coil a controller, and a high-power switching module. The controller is configured to generate low voltage control signals for administering a treatment protocol via the coil. The high-power switching module is configured to generate a high voltage current delivered to the coil based on the low voltage control signals. In some embodiments, the high-power switching module includes a printed circuit board used to reduce intrinsic resistance and parasitic capacitance of the circuit such that the current delivered to the coil over a sequence of bursts remains stable. A new protocol for administering transcranial magnetic stimulation, referred to as high-density Theta Burst Stimulation (hdTBS), utilizes a pulse frequency of at least 40 Hz and a number of pulses per burst of four or greater.

20 Claims, 8 Drawing Sheets

120

(56) References Cited

U.S. PATENT DOCUMENTS

| | | | | |
|---|---|---|---|---|
| 2007/0080360 | A1* | 4/2007 | Mirsky | H10H 20/858 257/706 |
| 2011/0152967 | A1* | 6/2011 | Simon | A61N 2/006 607/45 |
| 2016/0184601 | A1* | 6/2016 | Gleich | A61N 2/02 600/14 |
| 2019/0201707 | A1 | 7/2019 | Stubbeman | |
| 2020/0324133 | A1* | 10/2020 | Schwarz | A61N 2/02 |

OTHER PUBLICATIONS

Huang et al., "Theta Burst Stimulation of the Human Motor Cortex Neuron," *Neuron*, 45: 201-206 (2005).

Peterchev et al., "Controllable pulse parameter transcranial magnetic stimulator with enhanced circuit topology and pulse shaping," *J. of Neural Engineering*, 11(5): 056023 (2014) (Author Manuscript).

Peterchev et al., "Repetitive transcranial magnetic stimulator with controllable pulse parameters," *J. Neural Eng.* 8(3): 036016 (2011) (Author Manuscript).

Thut et al., "A Review of Combined TMS-EEG Studies to Characterize Lasting Effects of Repetitive TMS and Assess Their Usefulness in Cognitive and Clinical Neuroscience," *Brain Topography*, 22(4): 219-232 (2010) (Author Manuscript).

Peterchev et al., "A Novel Transcranial Magnetic Stimulator Inducing Near Rectangular Pulses with Controllable Pulse Width (cTMS)," IEEE Trans Biomed Eng.; 55(1): 257-266 (Jan. 2008).

Cole et al., "Stanford Neuromodulation Therapy (SNT): A Double-Blind Randomized Controlled Trial," Am J Psychiatry 179:2, 132-139: (Feb. 2022).

Cole et al., "Stanford Accelerated Intelligent Neuromodulation Therapy for Treatment-Resistant Depression," Am J Psychiatry 177:8, 716-726: (Aug. 2020).

Meng et al., "A High-Density Theta Burst Paradigm Enhances the Aftereffects of Transcranial Magnetic Stimulation: Evidence from Focal Stimulation of Rat Motor Cortex," Brain Stimulation, vol. 15, Issue 3, pp. 833-842 (May-Jun. 2022).

Torrico-Bascopé et al., "A High Frequency Transformer Isolation 110V/220V Input Voltage UPS System," 21st Annual IEEE Applied Power Electronics Conference and Exposition, APEC '06 (Mar. 2006).

Wendt et al., "The effect of pulse shape in theta-burst stimulation: Monophasic vs biphasic TMS," Brain Stimulation, vol. 16, Issue 4, pp. 1178-1185 (Jul.-Aug. 2023).

* cited by examiner

PROTOCOL TO ENHANCE THERAPEUTIC EFFECTS OF TRANSCRANIAL MAGNETIC STIMULATION

CROSS-REFERENCE TO RELATED APPLICATIONS

This application claims priority to U.S. Provisional Patent Application No. 63/286,229, filed on Dec. 6, 2021, the disclosure of which is hereby incorporated by reference in its entirety.

STATEMENT REGARDING FEDERALLY SPONSORED RESEARCH OR DEVELOPMENT

This invention was made with Government support under project numbers ZIA DA000638-01 and ZIA DA000545-12 by the National Institutes of Health, National Institute on Drug Abuse. The Government has certain rights in the invention.

FIELD

The present disclosure relates to methods of treatment using transcranial magnetic stimulation (TMS). More specifically, the present disclosure describes a protocol for administering treatment sessions of TMS using a TMS coil and controller for generating a pulse train for the TMS coil.

BACKGROUND

Transcranial Magnetic Stimulation (TMS) is a non-invasive neuro-modulation technique that has recently been cleared by the FDA as a therapy for treatment-resistant major depression, obsessive-compulsive disorder (OCD), and/or nicotine addiction. Stimulation of a patient's brain is produced by passing a brief but strong electric current through a coil placed in close proximity to the patient's head, which generates an electric field inside the patient's brain, thereby exciting or inhibiting a targeted region of the brain. TMS is currently being studied for application to other neurological and/or psychiatric disorders.

A first protocol for administering TMS may be referred to as repetitive high-frequency TMS (rTMS), which administers pulses of current to the TMS coil at a frequency of 10 Hz. A cycle of the treatment energizes the coil during a period of 4 seconds and then deactivates the coil for 26 seconds, and 75 cycles are performed per treatment. Further, the length of time required to administer a treatment session is approximately 37.5 minutes.

Intermittent Theta Burst Stimulation (iTBS) is a newer protocol for administering TMS. Rather than delivering a single pulse at a fixed frequency of 10 Hz, iTBS delivers bursts of 3 pulses at a 50 Hz pulse frequency, with an inter-burst interval of 200 ms (e.g., 5 Hz). A cycle of the treatment energizes the coil during a period of 2 seconds (which may be referred to as a burst train) and then deactivates the coil for 8 seconds per cycle, thereby defining an inter-train interval of 10 seconds, and 20 cycles are performed per treatment session delivering 30 pulses per 2 second burst train for a total of 600 pulses per treatment session.

A treatment time of administering a session of iTBS compared to rTMS is reduced from approximately 37.5 minutes to a little over 3 minutes, making iTBS much more tolerable to a patient due to the shortened nature of the treatment. However, as the pulses of current are generated at much higher frequency (e.g., 50 Hz instead of 10 Hz), the iTBS protocol is more challenging to implement from a hardware perspective with the high voltages and currents required (e.g., 2-3 kV and 3-6 kA to induce supra-threshold stimulation).

Conventionally, the controller for producing the current transmitted to the coil is implemented using large semiconductor switch modules connected via large copper cables or bus bars. The parasitic inductance intrinsic in these circuits induces transient voltage overshoots. For example, With a 150 nH capacitor bank series inductance, a 23-kV transient voltage overshoot was estimated on an insulated gate bipolar transistor (IGBT) with a 10-nF collector capacitance if the coil current reached 6 kA (Peterchev et al., "A transcranial magnetic stimulator inducing near-rectangular pulses with controllable pulse width (cTMS)." J. Neural Eng. 2008; 55(1):257-265). Such transient voltage overshoot can readily reach the maximum voltage rating of the components and devices, causing circuit breakdown; it also raises safety concerns to experimental subjects as well.

Additionally, intrinsic resistance in the TMS control circuit causes energy loss resulting from Joule heating. For example, a square pulse with electric current I=3000 A, a pulse duration of T=200 μs, and a resistance of R=0.1Ω will cause an energy loss $I^2$ RT=180 Joules. Energy loss is particularly critical when TMS pulses are delivered at high frequency, such as with the iTBS protocol.

Conventional controller hardware, such as that described above, made it difficult to administer a TMS protocol with more pulses or at higher frequencies than that of the rTMS or iTBS protocols. However, the efficacy of the conventional rTMS or newer iTBS protocols remain modest, and a newer protocol that achieves both high efficacy and high time-efficiency is of great clinical significance.

SUMMARY

Embodiments of the present disclosure relate to a protocol to enhance therapeutic effects of transcranial magnetic stimulation. Systems and methods are disclosed for treating various conditions such as treatment-resistant depression and obsessive-compulsive disorder using a high-density theta burst stimulation (hdTBS) protocol.

In accordance with a first aspect of the present disclosure, a system for delivering current to a coil is provided. The system includes a coil, a low-voltage controller, and a high-power switching module. The low-voltage controller generates low voltage control signals, and the high-power switching module is configured to generate a high voltage current delivered to the coil based on the low voltage control signals. The controller is configured to cause, through the low voltage control signals, the high-power switching module to generate a plurality of bursts of pulses of current through the coil, wherein a pulse frequency of each burst of pulses is at least 40 Hz and a number of pulses per burst is at least four.

In an embodiment of the first aspect, the low voltage control signals include an enable signal, an inhibit signal, at least one amplitude signal, and at least one pulse width and frequency signal.

In an embodiment of the first aspect, each amplitude signal of the at least one amplitude signal is generated by a digital-to-analog converter (DAC) that converts a pulse width modulation signal generated by a microcontroller into a voltage. Each pulse width and frequency signal of the at least one pulse width and frequency signal is generated by a gate driver.

In an embodiment of the first aspect, the microcontroller is coupled to at least one processor and a display device.

In an embodiment of the first aspect, the high-power switching module includes a power supply unit, a capacitor, a first switch device configured to enable charging of the capacitor by the power supply unit, an insulated gate bipolar transistor (IGBT), a diode, a first resistor connected in series with the diode, a second resistor, and a second switch device connected in series with the second resistor and configured to enable the capacitor to discharge through the second resistor.

In an embodiment of the first aspect, the high-power switching module includes two power supply units and two IGBTs configured to deliver biphasic pulses to the coil.

In an embodiment of the first aspect, the capacitor, the IGBT, the diode, and the first resistor are connected to a multi-layer printed circuit board.

In an embodiment of the first aspect, the multi-layer printed circuit board includes at least seven layers including a top metal layer, a bottom metal layer, an interior ground plane metal layer, and an interior high-voltage plane metal layer. Each of the metal layers separated by a dielectric layer.

In an embodiment of the first aspect, the pulse frequency is 45 Hz. In another embodiment of the first aspect, the pulse frequency is 50 Hz.

In an embodiment of the first aspect, the number of pulses per burst is 4. In another embodiment of the first aspect, the number of pulses per burst is 6.

In an embodiment of the first aspect, the plurality of bursts of pulses of current are generated through the coil in a plurality of burst trains, each burst train having a duration of two seconds. One burst train is delivered to the coil every ten seconds.

In an embodiment of the first aspect, a total number of pulses delivered during a treatment session is at least 600.

In accordance with a second aspect of the present disclosure, a method is provided for administering transcranial magnetic stimulation to a patient via a high-density Theta Burst Stimulation (hdTBS) protocol. The method includes: providing a coil placed proximate a head of the patient; and generating a plurality of bursts of pulses of current through the coil. A pulse frequency of each burst of pulses is at least 40 Hz and a number of pulses per burst is at least four.

In an embodiment of the second aspect, the pulse frequency is 45 Hz. In another embodiment of the second aspect, the pulse frequency is 50 Hz.

In an embodiment of the second aspect, the number of pulses per burst is 4. In another embodiment of the second aspect, the number of pulses per burst is 6.

In an embodiment of the second aspect, the coil is connected to a high-power switching module that generates current through the coil in accordance with low-voltage control signals generated by a controller. The high-power switching module includes a power supply unit, a capacitor, a first switch device configured to enable charging of the capacitor by the power supply unit, an insulated gate bipolar transistor (IGBT), a diode, a first resistor connected in series with the diode, a second resistor, and a second switch device connected in series with the second resistor and configured to enable the capacitor to discharge through the second resistor.

An object of the embodiments of the present disclosure described herein is to increase efficacy of TMS treatments using a new paradigm while maintaining a short length of a treatment session similar or better than that of the iTBS protocol. The objective may be enabled through use of a high-power switching module that utilizes a multi-layered printed circuit board (PCB) to implement a circuit for generating high voltage, high current pulses to the coil. The PCB reduces the intrinsic resistance and parasitic capacitance of the circuit such that the number of pulses in a burst can be increased while still maintaining a stable pulse shape.

BRIEF DESCRIPTION OF THE DRAWINGS

The present systems and methods for administering transcranial magnetic stimulation (TMS) are described in detail below with reference to the attached figures.

DETAILED DESCRIPTION

A protocol for delivering transcranial magnetic stimulation (TMS) is provided herein, which may be referred to as high-density Theta Burst Stimulation (hdTBS). The hdTBS protocol increases the number of pulses per burst from three in the iTBS protocol to four, five, six, or more pulses per burst while maintaining a 200 ms inter-burst interval. In some embodiments, the pulse frequency is defined as more than 40 Hz and, in particular, may be at least 45 Hz and, in some cases, may be 50 Hz. A total treatment session may be, e.g., 600 pulses, which in the case of 6 pulses per burst, would take approximately 100 seconds to administer using a 2 second burst train and 10 second inter-train interval. In other embodiments, the number of pulses per treatment session can be varied (e.g., 1,800 pulses per treatment session).

In order to facilitate the administration of a treatment session with the hdTBS protocol, a system is disclosed that includes a low-voltage controller and a high-power switching module that generates a high-voltage current provided to a coil based on a set of low-voltage control signals generated by the controller. The controller may be used to set various parameters of the treatment session including, but not limited to, a pulse frequency, a pulse duration, a number of pulses per burst, an inter-burst interval, an inter-train interval, a total number of pulses per treatment session. In some embodiments, the low-voltage control signals are optically isolated from the high-voltage circuit to improve safety of the system.

In an embodiment, the high-power switching module includes a printed circuit board (PCB) bus that includes a multi-layer PCB. At least two interior metal layers of the PCB are utilized as a ground plane and a high-voltage distribution layer. Electrical components including a capacitor, an IGBT, a diode, and a resistor may be soldered to the PCB and connected to the high-voltage distribution layers in the interior of the PCB. The design of the PCB facilitates a low intrinsic capacitance and low resistance associated with the circuit configured to generate the high-voltage current for the coil, thereby enabling the high-power pulses to be accurately delivered to the coil.

The efficacy of the hdTBS protocol was assessed in the motor cortex of rats using a recently developed rodent-specific coil. Results demonstrate that, in comparison to conventional iTBS, hdTBS enhances the aftereffects by a factor of 2 while maintaining the same time-efficiency. Human clinical trials of the hdTBS protocol are currently being pursued to confirm the results from the rodent studies.

Figure 1:
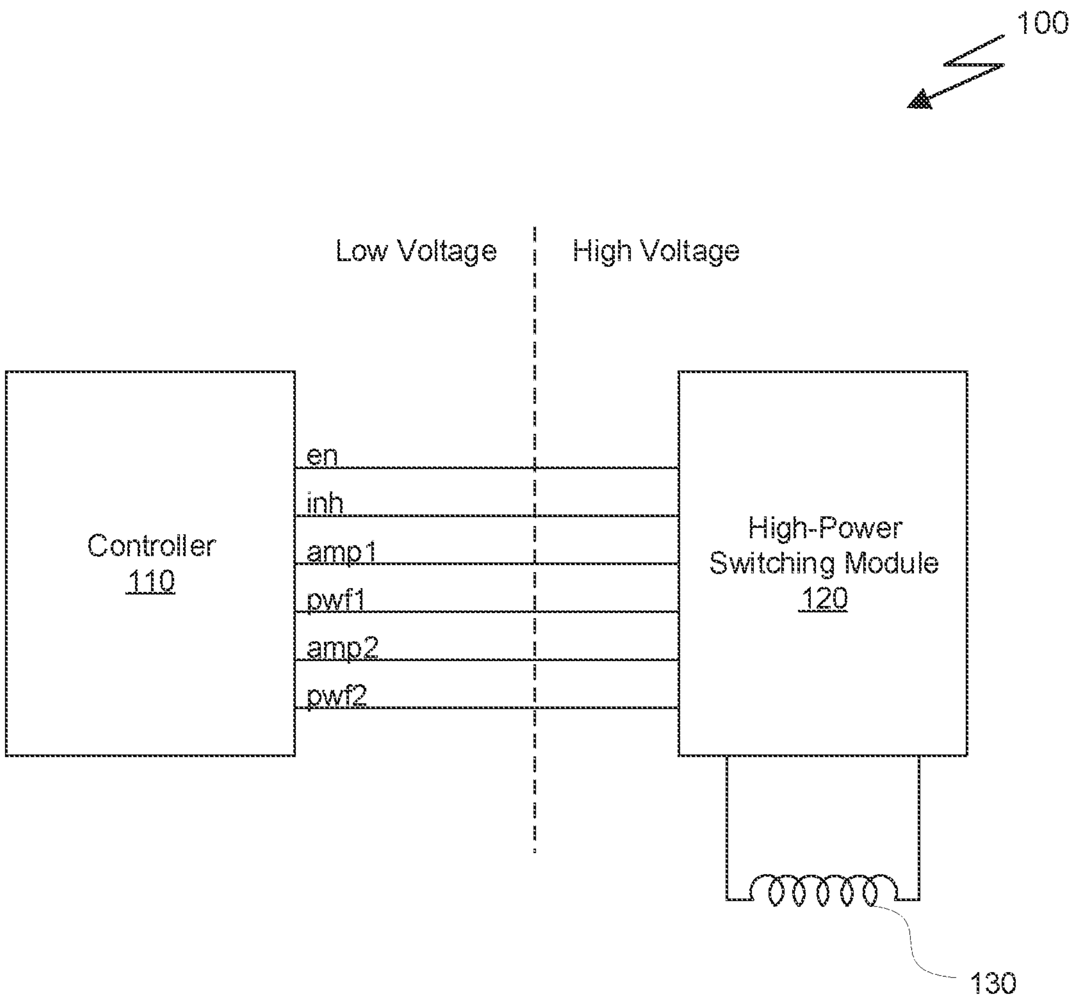
FIG. 1 illustrates a schematic of a system for administering transcranial magnetic stimulation, in accordance with an embodiment.

FIG. 1 illustrates a schematic of a system 100 for administering transcranial magnetic stimulation, in accordance with an embodiment. As depicted in FIG. 1, the system 100 includes a controller 110, a high-power switching module 120, and a coil 130. The controller 110 operates in a low voltage domain and the high-power switching module 120 and the coil 130 operate in a high voltage domain. The controller 110 is configured to generate a set of low-voltage signals that are transmitted to the high-power switching module 120. These signals operate to generate pulses of current transmitted through the coil 130 in accordance with a particular TMS protocol.

In accordance with an embodiment, the controller 110 generates six control signals: an enable signal (en), an inhibit signal (inh), a first amplitude signal (amp1), a first pulse width and frequency signal (pwf1), a second amplitude signal (amp2), and a second pulse width and frequency signal (pwf2). The first and second amplitude signals and first and second pulse width and frequency signals are utilized to implement biphasic pulses of current supplied to the coil 130. In other embodiments, a single amplitude signal and a single pulse width and frequency signal can be utilized to implement monophasic pulses of current supplied to the coil 130.

The high-power switching module 120 takes the low-voltage control signals and generates the high voltage (e.g., ~1-3 kV) and high current (e.g., ~1-4 kA) pulses supplied to the coil 130. As will be discussed in more detail below, administering TMS treatment using a high-density Theta Burst Stimulation (hdTBS) protocol includes generating current pulses at a frequency of 45 Hz (e.g., 22 ms inter-pulse duration) with a pulse duration of approximately 200 μs. A number of pulses are delivered in a burst (e.g., 3, 4, 5, or 6 pulses), and an inter-burst duration of 200 ms (e.g., 5 Hz). A treatment session consists of applying a burst train for a number of seconds and then keeping the coil inactive for a number of seconds. For example, a burst train may be administered to the patient for 4 seconds, and then the coil 130 remains inactive for 6 seconds, such that a new burst train is generated every ten seconds and is four seconds in duration. The total treatment session can last approximately 200 seconds, delivering 1000 bursts corresponding to between 3000 and 6000 pulses per treatment session. In other embodiments, the pulse frequency may be 50 Hz (e.g., 20 ms inter-pulse duration).

Figure 2:
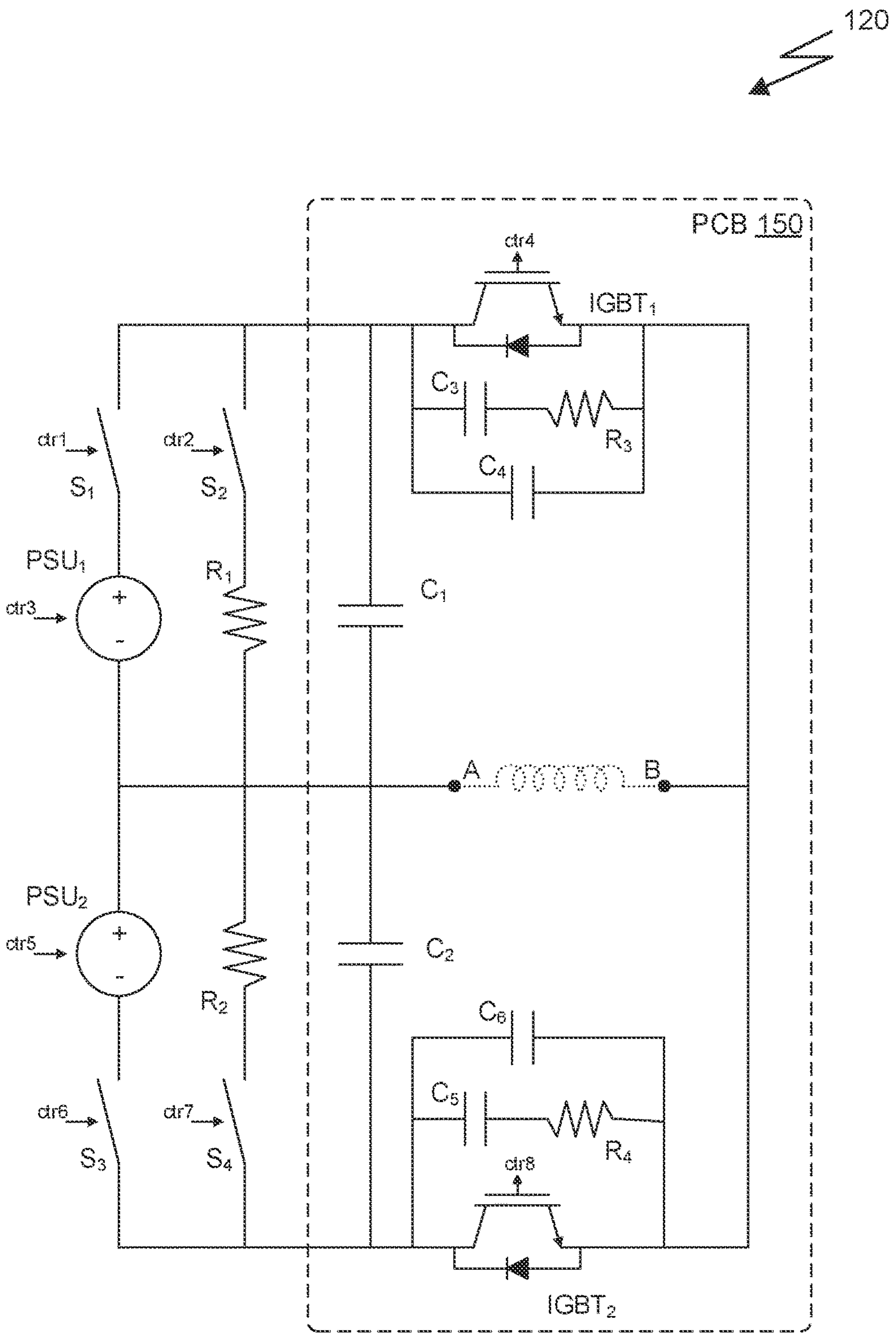
FIG. 2 is a schematic diagram of the high-power switching module for generating a current supplied to the coil of the system of FIG. 1, in accordance with an embodiment.

FIG. 2 is a schematic diagram of the high-power switching module 120 for generating a current supplied to the coil 130 of the system 100 of FIG. 1, in accordance with an embodiment. The high-power switching module 120 includes two power supply units (PSUs) connected in series to generate electricity to charge a pair of capacitors coupled to a printed circuit board (PCB) bus 150. The circuit may be divided into an upper portion of the circuit used to control the positive voltage phase of the pulse current and a lower portion of the circuit used to control the negative voltage phase of the pulse current. The following describes the operation of the upper portion of the circuit.

As depicted in FIG. 2, a negative terminal of a first power supply unit ($PSU_1$) is connected to a common node and a positive terminal of the first $PSU_1$ is connected to a switching device ($S_1$). The switching device is controlled by a first control signal (ctr1) and, when activated, causes $PSU_1$ to supply a positive voltage to the first capacitor ($C_1$), thereby charging $C_1$. A first insulated gate bipolar transistor ($IGBT_1$) is utilized to connect $C_1$ across the coil 130 at terminals A,B. It will be appreciated that the coil 130 is shown as a dotted line because the coil 130 is not directly fixed to the PCB bus 150, but instead is connected via cable attached to terminals attached to the PCB bus 150.

In addition to $IGBT_1$, a snubber circuit is included across the drain and source terminals of the transistor. The snubber circuit includes a first capacitor ($C_3$) in series with a resistor ($R_3$) and a second capacitor ($C_4$) in parallel with both capacitor $C_3$ and resistor $R_3$. In some embodiments, capacitor $C_4$ can be omitted leaving only a single current path in the snubber circuit. Once the circuit is enabled, current will flow through the snubber circuit in response to transient voltage spikes caused by abrupt changes in the magnetic field of the coil 130 when the transistor $IGBT_1$ is switched on and off.

In order to deactivate the high-power switching module 120, a second switching device ($S_2$) can be activated via a second control signal (ctr2) to discharge capacitor $C_1$ through a first resistor ($R_1$). This can allow the circuit to be de-energized without having to discharge capacitor $C_1$ through the coil 130.

The voltage of the $PSU_1$ can be controlled via a third control signal (ctr3) (e.g., 0-5 VDC can cause the voltage-controlled power supply to generate power between 0 and 5 kV up to a maximum current). Finally, the pulse duration and frequency of pulses can be controlled by a fourth control signal (ctr4) that is connected to a gate of the transistor $IGBT_1$. The length of time that the gate terminal of transistor $IGBT_1$ is activated controls the pulse duration, and the time between activating the gate terminal controls the pulse frequency.

The lower portion of the circuit operates in a similar manner to the upper portion, except to supply the coil 130 with a negative voltage current generated by a second power supply unit ($PSU_2$) (i.e., the direction of current through the coil 130 is reverse compared to the direction of current controlled by the upper portion of the circuit). The voltage of the $PSU_2$ can be controlled via a fifth control signal (ctr5). A sixth control signal (ctr6) is coupled to a third switching device ($S_3$), which is activated to charge a second capacitor ($C_2$) via a voltage generated by a second power supply unit ($PSU_2$).

A second insulated gate bipolar transistor ($IGBT_2$) is utilized to connect $C_2$ across the coil 130 at terminals A,B. A snubber circuit, including capacitors $C_5$, $C_6$ and resistor $R_4$, is also attached across the drain and source terminals of the transistor $IGBT_2$ such that any positive voltage generated by the coil 130 when transistor $IGBT_2$ is turned off flows through the snubber circuit. In order to deactivate the high-power switching module 120, a fourth switching device ($S_4$) can be activated via a seventh control signal (ctr1) to discharge $C_2$ through a second resistor ($R_2$). The pulse duration and frequency of pulses can be controlled by an eighth control signal (ctr8) that is connected to a gate of the transistor $IGBT_2$.

In an embodiment, the switching devices (S1-S4) may be solid state relays or the like. The IGBTs should be selected to be capable of handling a current discharge of thousands of Amperes (e.g., 3 kA) and thousands of Volts (e.g., 3 kV) for short durations (e.g., 100-300 μs).

Figure 3:
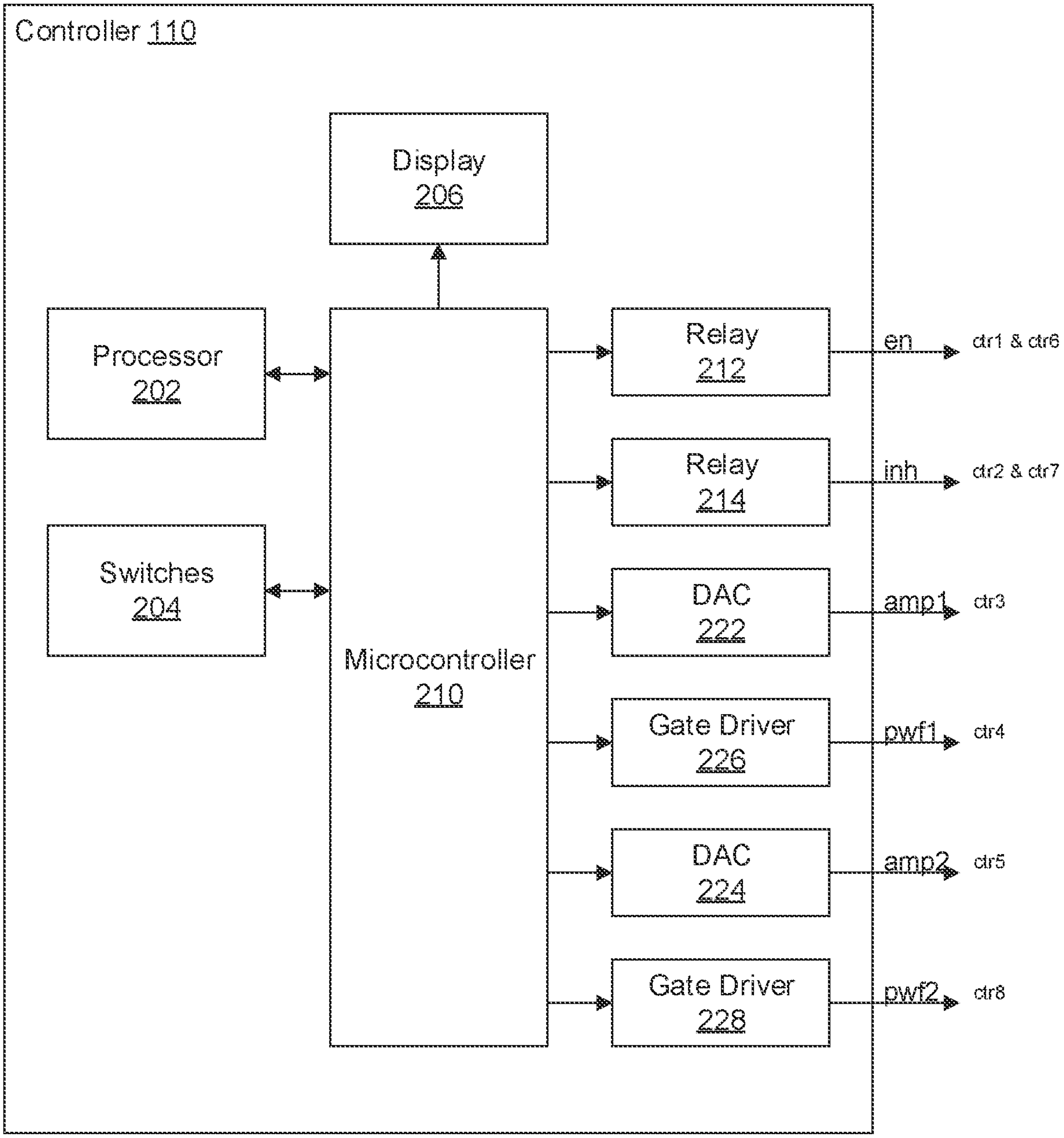
FIG. 3 is a block diagram of the controller for generating control signals for the high-power switching module of FIG. 2, in accordance with an embodiment.

FIG. 3 is a block diagram of the controller 110 for generating control signals for the high-power switching module 120 of FIG. 2, in accordance with an embodiment. As depicted in FIG. 3, the controller 110 includes a processor 202, switches 204, a display 206, a microcontroller 210, relays 212, 214, digital-to-analog converters (DAC) 222, 224, and gate drivers 226, 228. Although not shown explicitly in FIG. 3, the controller 110 may also include one or more memory devices including volatile memory (e.g., dynamic random access memory (DRAM)) and/or non-volatile memory (e.g., electrically erasable programmable read only memory (EEPROM), flash memory, hard disk drives (HDD), solid state drives (SSD), or the like). The processor 202 and microcontroller 210 may each include a separate and distinct memory device and/or may share an external memory device or may each be coupled to a separate and distinct external memory device.

In an embodiment, the processor 202 is an embedded processor such as a reduced instruction set computer (RISC) processor. The processor 202 may be coupled to the microcontroller via a bus. In another embodiment, the processor 202 is a central processing unit such as an Intel x86-based CPU. The processor 202 may include one core or multiple cores and can be multi-threaded or hyper-threaded. In some embodiments, the processor 202 executes a real-time operating system designed to guarantee timely execution of instructions. Although the controller 110 is shown as including a single processor 202, in some embodiments, the controller 110 can include two or more processors or may include an accelerator device such as a graphics processing unit (GPU) or tensor processing unit (TPU) designed to operate asynchronously from the host processor (e.g., processor 202).

In an embodiment, the processor 202 is coupled to a microcontroller 210. The microcontroller 210 can be an ATmega328P device manufactured by Microchip Technology (Previously Atmel Corporation), or the like. The ATmega328P is a low-power CMOS 8-bit microcontroller based on a RISC architecture instruction set. In one embodiment, the processor 202 executes asynchronous code that controls an outer loop of a control algorithm. The processor 202 transmits signals to the microcontroller 210 that specify various parameters for generating the control signals to send to the high-power switching module 120. The microcontroller 210 then generates the control signals in real-time, enabling highly accurate timing of the pulse train that would not be possible based on signals generated by the processor 202 alone. In addition to the outer loop of the control algorithm, the processor 202 may also execute other processes, such as an operating system, one or more applications, and a graphical user interface (GUI) to be displayed on the display device 206.

Although not shown explicitly in FIG. 3, the controller 110 can also include one or more input devices such as a keyboard or mouse configured to provide feedback to the processor 202. The input devices may allow an operator to provide input that indicates parameters for a treatment session (e.g., such as specifying the number of pulses per burst, pulse frequency, burst frequency, session duration, voltage amplitude, pulse duration, etc.) as well as to start and/or stop a treatment session.

As an alternative to relying on a GUI and/or input device to control the administration of a treatment session, the controller 110 may include a number of switches 204, which may include DIP switches, toggle switches, buttons, or the like. The switches 204 may allow for the user/operator to select the appropriate parameters for the treatment session and initiate and/or stop the treatment session.

In one embodiment, the microcontroller 210 generates the control signals for the high-power switching module 120. As shown in FIG. 3, six output signals are generated by the microcontroller 210. The output signals control relays 212, 214, DACs 222, 224, and gate drivers 226, 228. A first relay 212 switches an enable signal (en) that corresponds with control of the switching devices $S_1$ and $S_3$ via control signals ctr1 and ctr6. A second relay 214 switches an inhibit signal (inh) that corresponds with control of the switching devices $S_2$ and $S_4$ via control signals ctr2 and ctr1. A first DAC 222 is used to generate an amplitude signal (amp1) for power supply $PSU_1$ via control signal ctr3, and a second DAC 224 is used to generate an amplitude signal (amp2) for power supply $PSU_2$ via control signal ctr5. The DACs 222, 224 receive a pulse-width modulation (PWM) signal from the microcontroller 210 and convert the PWM signal into a voltage (e.g., between 0 and 5 VDC). A first gate driver 226 is used to generate a pulse width and frequency signal (pwf1) for transistor $IGBT_1$ via control signal ctr4, and a second gate driver 228 is used to generate a pulse width and frequency signal (pwf2) for transistor $IGBT_2$ via control signal ctr8. The timing of switching the gate drivers 226,228 controls both the pulse width and the pulse frequency of the current supplied to the coil 130. In an embodiment, the low voltage control signals can be optically isolated from the high-voltage circuit.

It will be appreciated that the ability to generate pulses of current for the coil 130 is not a simple task. The current is generated at thousands of volts and thousands of amps for a small duration of time for each pulse. Such high power can cause significant heating in the components of the system. Furthermore, when pulse frequency is increased, the ability to charge the capacitors with enough charge to be able to supply the current for each pulse in the time between pulses can become challenging. Finally, in the prior art circuits, parasitic capacitance in the circuit can cause significant voltage overshoot to occur, making the pulse shape unstable. While generating three pulses at 50 Hz with 200 ms between burst was possible with the prior art circuits, extending the number of pulses beyond three pulses was difficult without changing the controller circuit. One solution to this issue may be addressed using a printed circuit board to reduce intrinsic resistance and parasitic capacitance of the circuit.

Figure 4:
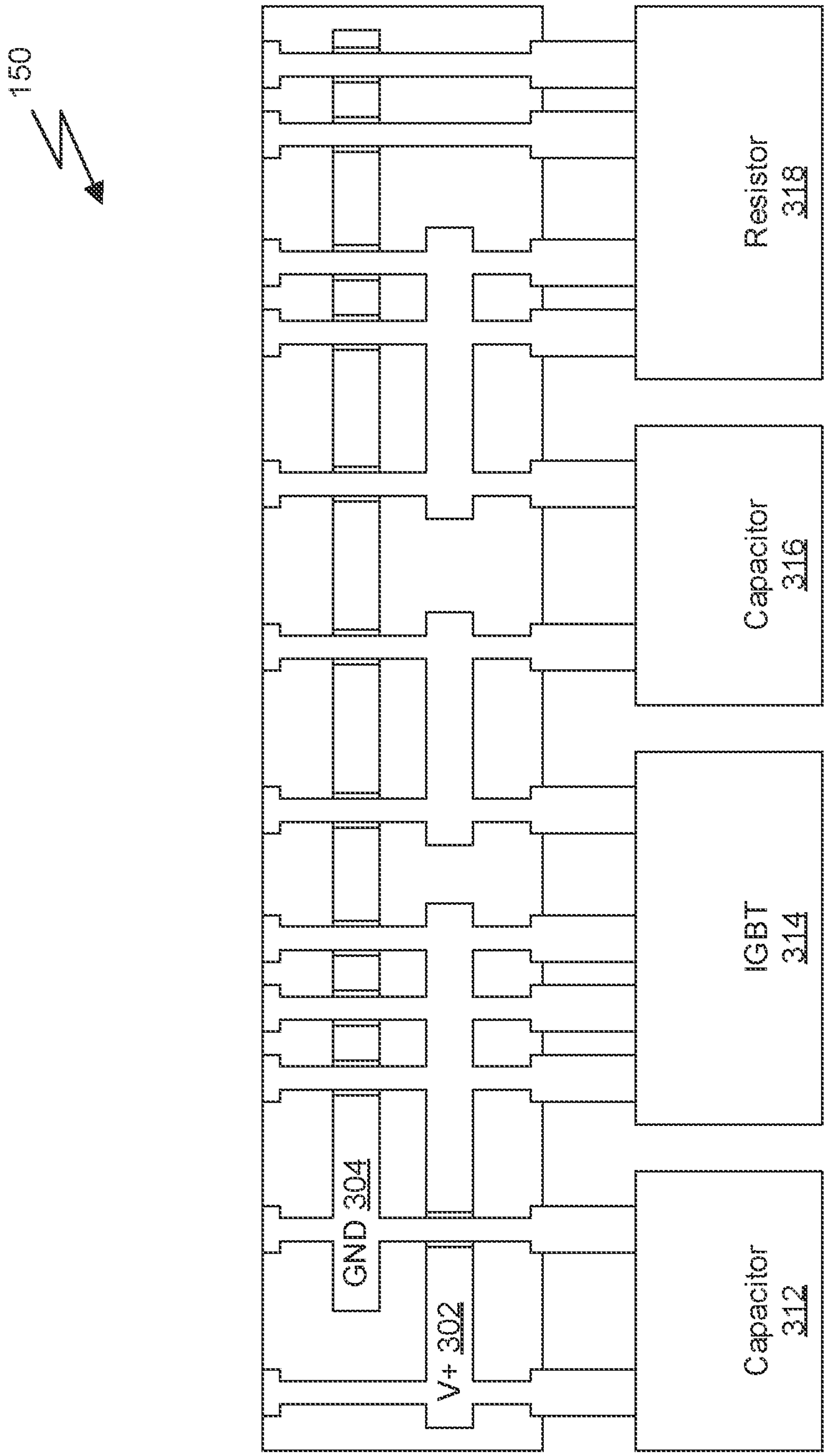
FIG. 4 illustrates the printed circuit board bus of FIG. 2, in accordance with an embodiment.

FIG. 4 illustrates the PCB bus 150 of FIG. 2, in accordance with an embodiment. The PCB bus 150 is a multi-layer circuit board having layers of metal (e.g., copper) interspersed between layers of dielectric material (e.g., FR-4). In an embodiment, the number of layers is seven, although additional layers, such as additional ground plane layers or signal routing layers, are contemplated as within the scope of the present disclosure.

As depicted in FIG. 4, the PCB bus 150 includes top and bottom metal layers having pads formed therein. Electrical components are soldered to the pads on the bottom metal layer. The electrical components can include a capacitor 312, an IGBT 314, a capacitor 316, and a resistor 318. It will be appreciated that, although only one set of electrical components is shown in FIG. 4, more than one set of electrical components can be connected to the PCB bus 150, such as to implement both the upper portion and the lower portion of the circuit in FIG. 2. Further, electrical components in addition to or in lieu of the electrical components shown herein may be coupled to the PCB bus 150. There are two additional metal layers within the interior of the PCB bus 150 for high voltage distribution. One layer 302 is provided for high-voltage signals including the positive voltage of the external power supply and any other intermediate signals such as between the capacitor 316 and the IGBT 314 and/or between the terminals of the coil 130 (not explicitly shown). The other layer 304 is a ground plane, which is connected to the negative voltage of the external power supply.

In addition to the four metal layers, three dielectric layers are disposed between each pair of adjacent metal layers. In an embodiment, the insulation between the high-voltage interior metal layers is sufficient to sustain up to 4.5 kV between the positive voltage plane 302 and the ground plane 304. Connections between layers can be achieved using vias (e.g., metal plated/filled holes in the PCB bus 150), and connections to the coil 130 and the external power supply can be made via the pads on the top layer of the PCB bus 150.

In one embodiment, the layout of the PCB bus 150 is effective to reduce the parasitic inductance to as low as 20 nH and a resistance to less than 0.1 ohm. These characteristics facilitate the administration of the hdTBS protocol.

Figure 5A:
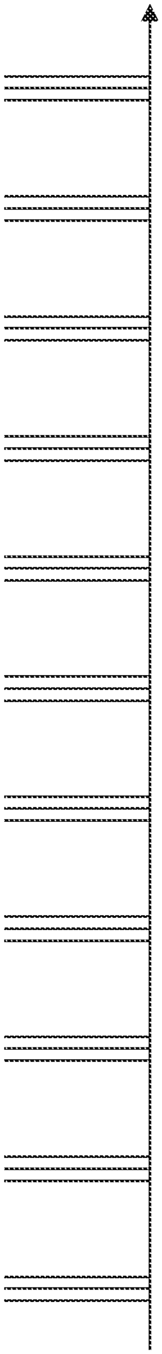
Fig. 5A (prior art)
FIG. 5A depicts a TMS protocol referred to as intermittent Theta Burst Stimulation (iTBS), in accordance with the prior art.
Figure 5B:
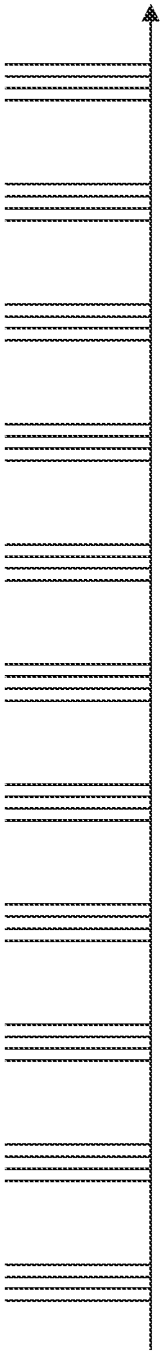
FIG. 5B depicts a high-density Theta Burst Stimulation (hdTBS) protocol having four pulses per burst, in accordance with an embodiment.
Figure 5C:
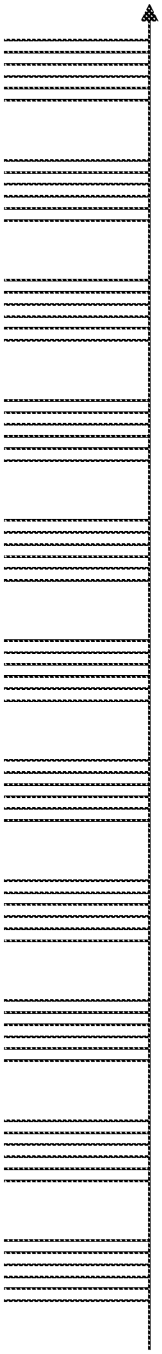
FIG. 5C depicts a hdTBS protocol having six pulses per burst, in accordance with another embodiment.

FIGS. 5A-5C illustrate various TMS treatment protocols. Again, a first protocol for administering TMS was to simply deliver pulses of current to the coil at a fixed frequency (e.g., 10 Hz), which is referred to as repetitive transcranial magnetic stimulation (rTMS). Subsequently, it was discovered that delivering pulses to the coil in bursts of three pulses, with a burst frequency of 5 Hz was potentially more effective at triggering a positive response in a subject. FIG. 5A depicts a TMS protocol referred to as intermittent Theta Burst Stimulation (iTBS), in accordance with the prior art.

The protocol for iTBS includes delivering bursts of three pulses of current to the coil at a pulse frequency of 50 Hz (e.g., 20 ms inter-pulse interval). After three pulses, the coil is deactivated for 160 ms, resulting in a burst frequency of 5 Hz (i.e., 200 ms inter-burst interval). Furthermore, a treatment session calls for 2 second burst trains, repeated at an inter-burst interval of ten seconds. In other words, ten bursts of 30 total pulses are delivered to the coil followed by deactivating the coil for eight seconds. This is repeated for 200 seconds, for a total of 600 pulses of current being delivered to the coil. While iTBS has been found to be modestly successful at producing long-term potentiation-like (LTP) effects, there is a need to find alternative protocols that produce better results.

FIG. 5B depicts a high-density Theta Burst Stimulation (hdTBS) protocol having four pulses per burst, in accordance with an embodiment. It is suggested that while the 200 ms inter-burst interval may be important for producing the desired effects in a patient, that increasing the number of pulses per burst could increase the LTP effects compared to the conventional iTBS protocol. In an embodiment, the protocol for hdTBS includes delivering bursts of four (or more) pulses of current to the coil at a pulse frequency of 45 Hz (e.g., 22 ms inter-pulse interval). After four pulses, the coil is deactivated for a period of time, resulting in a burst frequency of 5 Hz. In an embodiment, a treatment session also operates on a series of cycles, each cycle including a 2 second burst train, repeated every ten seconds. In other embodiments, the treatment session can double the number of bursts per train such that the coil is activated for 4 seconds and deactivated for 6 seconds. In addition, although 45 Hz was used as the pulse frequency, in other embodiments, the pulse frequency can be set to be the same as iTBS at 50 Hz. In yet another embodiment, the burst train can be delivered continuously without deactivating the coil, although it will be appreciated that without the deactivation period, excessive heat buildup in the components of the system may occur.

FIG. 5C depicts a hdTBS protocol having six pulses per burst, in accordance with another embodiment. It will be appreciated that hdTBS may utilize 4, 5, 6, or more pulses per burst, and that the design of the controller, specifically, by reducing the parasitic inductance and resistance associated with the high-power switching module 120, enables these pulses to be delivered reliably compared to prior art solutions where additional bursts beyond three may result in unstable current being delivered to the coil.

Figure 6:
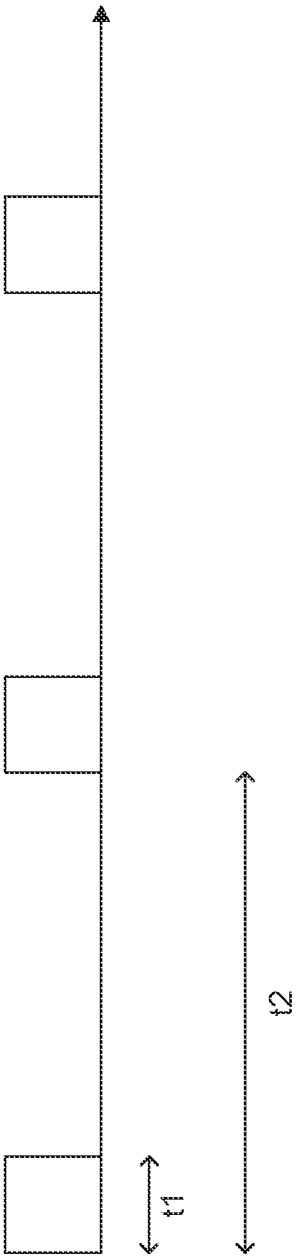
FIG. 6 illustrates a multi-cycle hdTBS protocol, in accordance with an embodiment.

FIG. 6 illustrates a multi-cycle hdTBS protocol, in accordance with an embodiment. As described above, rather than continuing to deliver a full complement of pulses in a continuous period with a constant inter-burst interval of 200 ms, the bursts can be delivered over a series of cycles, with each cycle defined as a first period during which the coil is energized followed by a second period during which the coil is de-energized.

As depicted in FIG. 6, in an embodiment, a cycle is defined as delivering a 2 second burst train during a first period of time (t1) and then deactivating the coil for a second period of time. A total cycle time (t2) is defined as 10 seconds, with the coil being energized during 2 of the 10 seconds. The cycle duration may also be referred to as an inter-train interval. In other embodiments, the first period of time may be increased to 4 seconds, while the inter-train interval is maintained at 10 seconds. Of course, in yet other embodiments, the inter-train interval may be varied as well (e.g., 5 seconds or 20 seconds).

Figure 7:
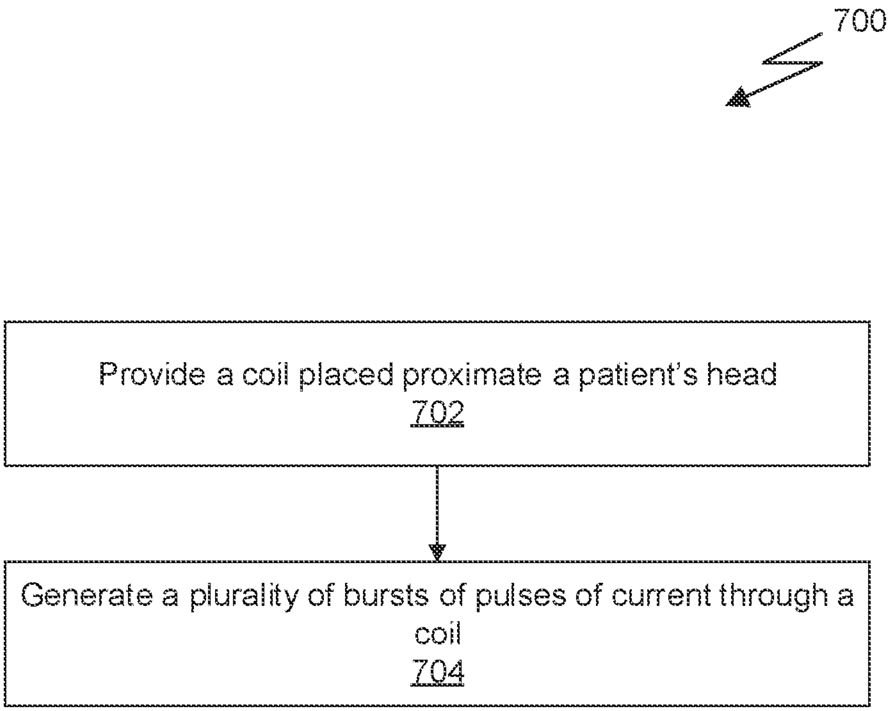
FIG. 7 is a flow diagram of a method for administering hdTBS to a patient, in accordance with an embodiment.

FIG. 7 is a flow diagram of a method 700 for administering hdTBS to a patient, in accordance with an embodiment. The method 700 can be performed utilizing the system 100 to administer the hdTBS treatment session.

At 702, a coil is placed proximate a subject's head and connected to the high-power switching module 120. The hdTBS treatment session may then be initiated using a set of parameters stored in a memory of the controller 110 and/or entered manually by a user via, e.g., a GUI and one or more input devices. The set of parameters can include, e.g., a pulse frequency, an inter-burst interval, a duration of a burst train, a total number of pulses per treatment session, and the like.

At 704, a plurality of bursts of pulses of current are generated through the coil. In an embodiment, the controller 110 is configured to automatically generate the pulses of current via a set of low-voltage control signals provided to a high-power switching module 120 connected to the coil 130. The control signals are operated in order to generate each pulse having a pulse duration, amplitude, and phase set according to a set of parameters. The control signals are also operated to generate bursts of pulses having a particular pulse frequency, number of pulses per burst (e.g., 4 or more pulses per burst), and inter-burst interval. In some embodiments, the control signals are also operated over a number of cycles to generate a burst train while activating the coil during a first period of time followed by a second period of time where the coil is deactivated. Multiple cycles are performed until a total number of pulses of current are delivered to the coil.

Figure 8:
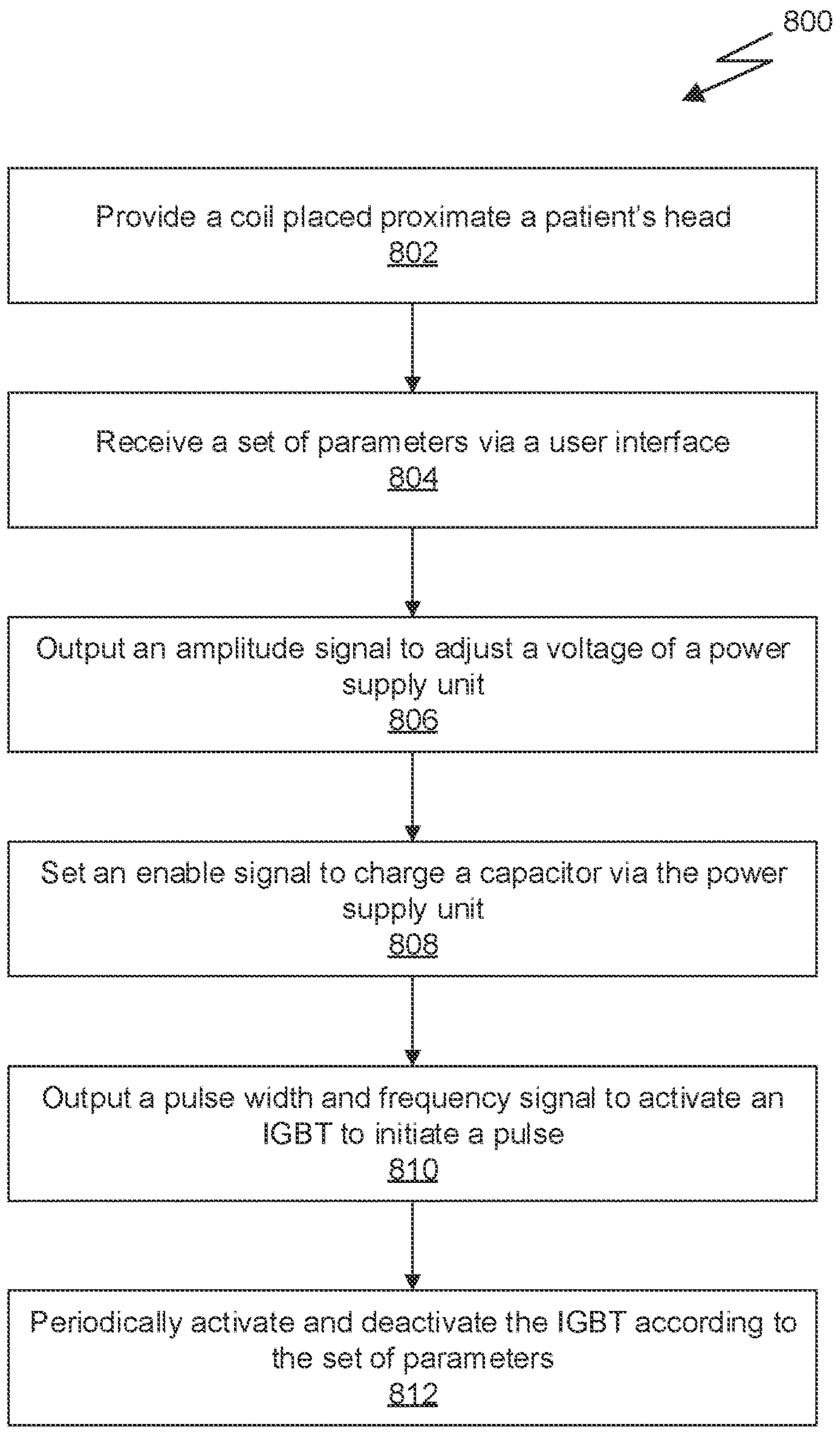
FIG. 8 is a flow diagram of a method for administering hdTBS to a patient, in accordance with another embodiment.

FIG. 8 is a flow diagram of a method 800 for administering hdTBS to a patient, in accordance with another embodiment. The method 800 can be performed utilizing the system 100 to administer the hdTBS treatment session.

At 802, a coil is placed proximate a subject's head and connected to the high-power switching module 120. Step 802 may be similar to step 702, and details are not described herein again.

At 804, a set of parameters are received via a user interface. In an embodiment, a user may use an input device to select parameters via a graphical user interface implemented by a controller 110. The user may vary a pulse frequency, a pulse duration, a number of pulses per burst, an amplitude of the pulse, an inter-burst interval, cycle duration, etc.

At 806, an amplitude signal is output to adjust a voltage of a power supply unit. In an embodiment, the controller 110 generates a pwm signal that is converted to a voltage signal that is transmitted to the high-power switching module. The voltage signal causes the power supply unit in the high-power switching module to adjust an output voltage of the power supply unit. In an embodiment, where biphasic pulses are to be generated by the high-power switching module 120, multiple amplitude signals may be generated for two power supply units, where one amplitude signal adjusts a positive voltage of the pulse and a second amplitude signal adjusts a negative voltage of the pulse.

At 808, an enable signal is set to charge a capacitor via the power supply unit. In an embodiment, the enable signal causes a switching device to close and connect the power supply unit to a capacitor connected to the PCB bus 150.

At 810, a pulse width and frequency signal is output to activate an IGBT to initiate a pulse of current through the coil. The pulse width and frequency signal causes the gate of the IGBT to permit current to flow from the capacitor through the coil, The pulse duration is controlled by the timing of the pulse width and frequency signal.

At 812, the IGBT is periodically activated and deactivated according to the set of parameters. The hdTBS protocol is performed by causing bursts of pulses of current to be transmitted through the coil at a timing defined by the protocol.

Longitudinal Motor-Invoked Potential (MEP) in Rats

MEP, a measure of electromyographic (EMG) signal in the activated muscle induced by stimulation of the corresponding motor cortex, has been traditionally employed as the metric to quantitatively and conveniently assess TMS effects. While an EMG signal can be readily acquired in humans using a surface electrode, consistent EMG recording in an awake rat is more challenging, since rats do not readily comply with a requirement for reducing motion. A rodent EMG recording approach is detailed below EMG electrodes were constructed of a soft 7-strand stainless steel microwire, 0.025 mm in diameter. The electrodes were cut into lengths of 13 cm; insulation coat from one end of the wire was stripped for 3 mm, and press-connected to a female socket. Two or more sockets were inserted into a 6-channel electrode pedestal. The pedestal and the microwires were attached to a circular Marlex mesh and secured with dental cement. A small portion (about 2 mm) of the insulation coat, 5 cm away from the other end, was carefully stripped. This de-insulated portion was the active contact to sense the EMG signal.

Rats were anesthetized using isoflurane and electrodes were implanted in the rats. One incision was made in the posterior trunk; a second incision was made in the right hind limb to expose the biceps femoris and gastrocnemius and was flushed with a gentamicin solution. Two microelectrode wires were passed subcutaneously from the posterior trunk incision to the hindlimb incision. The microelectrodes were then individually secured to a curved, open ended suture needle. Using the suture needle, one microelectrode was implanted into the Biceps Femoris ensuring that the uninsulated portion was situated within the muscle. The end of the microelectrode was then knotted five times to ensure it could not be pulled back through the muscle. A single suture through the muscle and around the knot was added for additional stability. The second microelectrode was implanted into the gastrocnemius using the same process. The back mount was then pushed through the posterior trunk incision until the mesh portion was underneath the skin with the connector rising out of the skin. Incisions were closed. After one week of surgical recovery, the microelectrodes were interfaced to a Biopac system via a 6-pin male connector. A standard EEG pad was connected to the tail to serve as ground electrode.

A focal TMS coil specific for a rodent brain was provided. The key to this novel design was the introduction of a small magnetic core that enhanced and focused the magnetic field generated by the coil. The high focality of this TMS coil raises a challenge for TMS administration, namely, how to consistently position the TMS to the region of interest in the rodent's brain. A strategy to address this question, namely implanting a headpost on the rat skull to serve as a reference and a detachable coil guide to efficiently position the TMS coil to the region of interest (e.g., a hindlimb motor cortex), was adopted in order to administer TMS to the rodents.

To mitigate animal stress during TMS administration, rats were habituated to the TMS environment for one week. A rodent-specific TMS coil with a sham setting (5% of the motor threshold) was used. Sham TMS was administered for 5 minutes per day with the rat held firmly underneath the coil. Fruit loops were given as a reward following the habituation session to reduce stress during training.

3D printed coil guides attached to the implanted headposts on awake rats were used to direct the focal point of the coil to the target region on the head surface. During administration, rats were held under the TMS coil for the full treatment session with the same holding method as habituation. Different TMS pulse paradigms were administered one session/day. Each session lasted for about 60 minutes, for a total of 7 days. MEP signal was consistently recorded from all rats for the duration of the experiment. Rats continued to receive Fruit Loops as a reward following treatment.

A total of 15 rats were used in this study. The study employed a within-subject cross-sessional design: for each rat, the number of pulses per burst was randomly assigned on a given day. MEP was measured by delivering single-pulse TMS. The inter-pulse interval was 5 second, with a total of 10 pulses. MEP was measured in the following time points: pre-TBS baseline, 5, 10, 15, 20, 25 and 35 min post-TBS. The amplitude of TMS pulses remained for MEP measurement, which was 100% of motor threshold pre-TBS administration.

All procedures were approved by the Animal Care and Use Committee of the National Institute on Drug Abuse, NIH.

Results of Animal Study

For a given coil, the magnetic field strength is proportional to coil current; temporal changes in magnetic field produce the desired electric field that excites or inhibits neuronal cells. Since energy loss is inevitable in pulse generation, a critical question is how stable the output current can be as the number of pulses per burst increases.

In the study, an inter-burst interval of 200 ms (i.e., 5 Hz) was utilized; an inter-pulse interval within each individual burst was 22 ms (i.e., 45 Hz). Current was output with the number of pulses per burst up to 6 pulses, and the output current was measured with an oscilloscope using a 1:1000 current probe. A consistent pulse waveform was seen across all 6 pulses. The first pulse had a peak-peak amplitude of +/−3 kiloamperes; the last one had +2.92/−2.88 kiloamperes. The maximum difference in pulse amplitude across the 6 pulses was 4%. As the number of pulses per burst increased to 7, unstable current output to the coil was detected, and, therefore, additional pulses per burst beyond 6 pulses was not further explored.

As a first step in evaluating the results of the hdTBS protocol, MEP was measured in the rat motor cortex. A single-pulse TMS was applied every 5 sec. With the head-post serving as the reference and the coil guide, the TMS coil was directed, as best as possible, to the rat motor cortex representation of the hindlimb region. To map the spatial focality of the coil, different coil guides were used to offset the positioning of the coil by 1 mm along 4 directions (rostral, caudal, left and right), and the MEP signal was measured at each location.

An MEP signal up to 1.6 mV peak-peak was detected with the coil aimed at the center of the hindlimb motor cortex; the amplitude diminished as we offset the coil by 1 mm. This data is consistent with a prior estimate: the rodent coil had a focality of 2 mm.

A question of whether that hdTBS protocol could enhance the neuromodulation effects was investigated. While brain response to TMS administration is of interest, it is the aftereffects that carry the therapeutic response and, therefore, are the most clinically relevant. Previous human TMS studies measured MEP signal pre- and post-TMS administration as a metric to assess the effects of TMS. A similar approach was adopted to evaluate hdTBS. The duration of the stimulation was kept constant (200 sec), while the number of pulses per burst varied. With 6 pulses per burst, apparent enhancement in MEP amplitudes was seen at 10 and 25 min post-TMS; in contrast, only modest enhancement was seen with 3 pulses per burst, which is consistent with conventional iTBS.

Variability in a baseline MEP signal was observed across animals and across days within the same animal. This is not unexpected, given that the specific locations of electrode implantation cannot be guaranteed to be identical across animals, and that electrode contact could experience minor displacement within leg muscles across days due to the animals' movement. Every attempt was made to normalize post-TMS MEP signal to the pre-TMS baseline, and statistical analysis was performed.

Compared with iTBS (i.e., 3 pulse per burst), significant enhancement in MEP amplitude was seen in hdTBS with 5 and 6 pulses per burst. This data is consistent with the notion that neuromodulation is sensitive to specific temporal patterns of TMS paradigms.

Further studies in human clinical trials are currently being pursued to confirm the experimental results in the animal studies and to assess the efficacy of the hdTBS protocol in human subjects for various conditions.

It is noted that the techniques described herein may be embodied in executable instructions stored in a computer readable medium for use by or in connection with a processor-based instruction execution machine, system, apparatus, or device. It will be appreciated by those skilled in the art that, for some embodiments, various types of computer-readable media can be included for storing data. As used herein, a "computer-readable medium" includes one or more of any suitable media for storing the executable instructions of a computer program such that the instruction execution machine, system, apparatus, or device may read (or fetch) the instructions from the computer-readable medium and execute the instructions for carrying out the described embodiments. Suitable storage formats include one or more of an electronic, magnetic, optical, and electromagnetic format. A non-exhaustive list of conventional exemplary computer-readable medium includes: a portable computer diskette; a random-access memory (RAM); a read-only memory (ROM); an erasable programmable read only memory (EPROM); a flash memory device; and optical storage devices, including a portable compact disc (CD), a portable digital video disc (DVD), and the like.

It should be understood that the arrangement of components illustrated in the attached Figures are for illustrative purposes and that other arrangements are possible. For example, one or more of the elements described herein may be realized, in whole or in part, as an electronic hardware component. Other elements may be implemented in software, hardware, or a combination of software and hardware. Moreover, some or all of these other elements may be combined, some may be omitted altogether, and additional components may be added while still achieving the functionality described herein. Thus, the subject matter described herein may be embodied in many different variations, and all such variations are contemplated to be within the scope of the claims.

To facilitate an understanding of the subject matter described herein, many aspects are described in terms of sequences of actions. It will be recognized by those skilled in the art that the various actions may be performed by specialized circuits or circuitry, by program instructions being executed by one or more processors, or by a combination of both. The description herein of any sequence of actions is not intended to imply that the specific order described for performing that sequence must be followed. All methods described herein may be performed in any suitable order unless otherwise indicated herein or otherwise clearly contradicted by context.

The use of the terms "a" and "an" and "the" and similar references in the context of describing the subject matter (particularly in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. Furthermore, the foregoing description is for the purpose of illustration only, and not for the purpose of limitation, as the scope of protection sought is defined by the claims as set forth hereinafter together with any equivalents thereof. The use of any and all examples, or exemplary language (e.g., "such as") provided herein, is intended merely to better illustrate the subject matter and does not pose a limitation on the scope of the subject matter unless otherwise claimed. The use of the term "based on" and other like phrases indicating a condition for bringing about a result, both in the claims and in the written description, is not intended to foreclose any other conditions that bring about that result. No language in the specification should be construed as indicating any non-claimed element as essential to the practice of the invention as claimed.

What is claimed is:

1. A system for administering transcranial magnetic stimulation, the system comprising:

a coil;

a controller configured to generate low voltage control signals; and a high-power switching circuit configured to generate a high voltage current delivered to the coil based on the low voltage control signals:

wherein the high-power switching circuit comprises a first portion and a second portion, wherein the first portion includes a first power supply unit, a first capacitor, and a first insulated gate bipolar transistor (IGBT), wherein the second portion includes a second power supply unit, a second capacitor, and a second IGBT, and wherein the first power supply unit is connected in series with the second power supply unit;

wherein the first power supply unit is connected in parallel with the first capacitor, and wherein the first power supply unit is connected in series with the first IGBT;

wherein the second power supply unit is connected in parallel with the second capacitor, and wherein the second power supply unit is connected in series with the second IGBT;

wherein the first IGBT and the second IGBT are configured to deliver biphasic pulses to the coil; and wherein the controller is configured to cause the high-power switching circuit to generate a plurality of bursts of pulses of current through the coil, wherein a pulse frequency of each burst of pulses is at least 40 Hz and a number of pulses per burst is at least four.

2. The system according to claim 1, wherein the low voltage control signals include an enable signal, an inhibit signal, at least one amplitude signal, and at least one pulse width and frequency signal.

3. The system according to claim 2, wherein each amplitude signal of the at least one amplitude signal is generated by a digital-to-analog converter (DAC) that converts a pulse width modulation signal generated by a microcontroller into a voltage, and wherein each pulse width and frequency signal of the at least one pulse width and frequency signal is generated by a gate driver.

4. The system according to claim 3, wherein the microcontroller is coupled to at least one processor and a display device.

5. The system according to claim 1, wherein the high-power switching circuit comprises:

a first switch device configured to enable charging of the first capacitor by the first power supply unit;

a diode;

a first resistor connected in series with the diode;

a second resistor; and a second switch device connected in series with the second resistor and configured to enable the first capacitor to discharge through the second resistor.

6. The system according to claim 5, wherein the first capacitor, the first IGBT, the diode, and the first resistor are connected to a multi-layer printed circuit board.

7. The system according to claim 6, wherein the multi-layer printed circuit board includes at least seven layers including a top metal layer, a bottom metal layer, an interior ground plane metal layer, and an interior high-voltage plane metal layer, each of the metal layers separated by a dielectric layer.

8. The system according to claim 1, wherein the pulse frequency is 45 Hz.

9. The system according to claim 8, wherein the number of pulses per burst is 4.

10. The system according to claim 8, wherein the number of pulses per burst is 6.

11. The system according to claim 1, wherein the pulse frequency is 50 Hz.

12. The system according to claim 1, wherein the plurality of bursts of pulses of current are generated through the coil in a plurality of burst trains, each burst train having a duration of two seconds, wherein one burst train is delivered to the coil every ten seconds.

13. The system according to claim 12, wherein a total number of pulses delivered during a treatment session is at least 600.

14. The system according to claim 1, wherein the low voltage control signals have a voltage of 5 V or less; and wherein the low-voltage control signals are optically isolated from the high-power switching circuit.

15. The system according to claim 1, wherein a first end of the first capacitor is connected to a first end of the first IGBT;

wherein a second end of the first capacitor is connected to a first end of the coil;

wherein a first end of the second capacitor is connected to a first end of the second IGBT;

wherein a second end of the second capacitor is connected to the first end of the coil;

wherein a second end of the first IBGT is connected to a second end of the coil; and wherein a second end of the second IBGT is connected to the second end of the coil.

16. A method for administering transcranial magnetic stimulation, comprising:

generating, by a controller, low voltage control signals;

generating, by a high-power switching circuit, a high voltage current delivered to a coil placed proximate a head of the patient based on the low voltage control signals; and generating, by the high-power switching circuit, a plurality of bursts of pulses of current through the coil, wherein a pulse frequency of each burst of pulses is at least 40 Hz and a number of pulses per burst is at least four;

wherein the high-power switching circuit comprises a first portion and a second portion, wherein the first portion includes a first power supply unit, a first capacitor, and a first insulated gate bipolar transistor (IGBT), wherein the second portion includes a second power supply unit, a second capacitor, and a second IGBT, and wherein the first power supply unit is connected in series with the second power supply unit;

wherein the first power supply unit is connected in parallel with the first capacitor, and wherein the first power supply unit is connected in series with the first IGBT;

wherein the second power supply unit is connected in parallel with the second capacitor, and wherein the second power supply unit is connected in series with the second IGBT;

wherein the first IGBT and the second IGBT are configured to deliver biphasic pulses to the coil.

17. The method according to claim 16, wherein the pulse frequency is 45 Hz.

18. The method according to claim 17, wherein the number of pulses per burst is 4.

19. The method according to claim 17, wherein the number of pulses per burst is 6.

20. The method according to claim 16, wherein the pulse frequency is 50 Hz.

* * * * *